US008128509B2

(12) United States Patent
Soracco et al.

(10) Patent No.: US 8,128,509 B2
(45) Date of Patent: *Mar. 6, 2012

(54) METAL WOOD CLUB WITH IMPROVED HITTING FACE

(75) Inventors: Peter L. Soracco, Carlsbad, CA (US); Scott A. Rice, San Diego, CA (US); Nicholas M. Nardacci, Bristol, RI (US)

(73) Assignee: Acushnet Company, Fairhaven, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/093,752

(22) Filed: Apr. 25, 2011

(65) Prior Publication Data
US 2011/0201450 A1   Aug. 18, 2011

Related U.S. Application Data

(63) Continuation of application No. 12/729,214, filed on Mar. 22, 2010, now Pat. No. 7,931,545, which is a continuation of application No. 11/370,542, filed on Mar. 8, 2006, now Pat. No. 7,682,262, which is a continuation-in-part of application No. 10/911,341, filed on Aug. 4, 2004, now Pat. No. 7,207,898, which is a continuation-in-part of application No. 10/428,061, filed on May 1, 2003, now Pat. No. 7,029,403, which is a continuation-in-part of application No. 09/551,771, filed on Apr. 18, 2000, now Pat. No. 6,605,007.

(51) Int. Cl.
*A63B 53/04* (2006.01)

(52) U.S. Cl. ........ 473/329; 473/342; 473/345; 473/346; 473/349

(58) Field of Classification Search .......... 473/287–292, 473/324–350
See application file for complete search history.

(56) References Cited

U.S. PATENT DOCUMENTS

| 1,318,325 | A | 10/1919 | Klin |
| 1,319,233 | A | 10/1919 | Mattern |
| 1,467,435 | A | 9/1923 | Kinnear |
| 1,525,352 | A | 2/1925 | Aitken |
| 1,543,691 | A | 6/1925 | Beat |
| 1,582,836 | A | 4/1926 | Link |
| 1,589,363 | A | 6/1926 | Butchart |
| 1,595,589 | A | 8/1926 | Tyler |

(Continued)

FOREIGN PATENT DOCUMENTS

CN   1114911   1/1996

(Continued)

OTHER PUBLICATIONS

Golf Digest, Sep. 1982, p. 25.

(Continued)

*Primary Examiner* — Sebastiano Passaniti
(74) *Attorney, Agent, or Firm* — Michael J. Mancuso

(57) ABSTRACT

A hitting face of a golf club head having improved flexural stiffness properties. In one embodiment, the hitting face is made from multiple materials. Each material has a different tensile modulus of elasticity, where the center of the hitting face has a much higher tensile modulus of elasticity than the surrounding portions of the hitting face. This creates a stiff center and a more easily deflected concentric portion. In another embodiment, the materials have different yield strengths and elongation, where the center of the hitting face has a very high yield strength compared to the surrounding portions of the hitting face.

20 Claims, 4 Drawing Sheets

U.S. PATENT DOCUMENTS

| | | |
|---|---|---|
| 1,605,551 A | 11/1926 | Mattern |
| 1,699,874 A | 1/1929 | Buhrke |
| 1,704,119 A | 3/1929 | Buhrke |
| 1,704,165 A | 3/1929 | Buhrke |
| 1,720,867 A | 7/1929 | Webster et al. |
| 2,034,936 A | 3/1936 | Barnhart |
| 2,087,685 A | 7/1937 | Hackney |
| 3,567,228 A | 3/1971 | Lynn |
| 3,571,900 A | 3/1971 | Hardesty |
| 3,625,518 A | 12/1971 | Solheim |
| 3,659,855 A | 5/1972 | Hardesty |
| 3,863,932 A | 2/1975 | Lezatte |
| 3,985,363 A | 10/1976 | Jepson et al. |
| 4,023,802 A | 5/1977 | Jepson et al. |
| 4,193,601 A | 3/1980 | Reid, Jr. et al. |
| 4,213,613 A | 7/1980 | Nygren |
| 4,214,754 A | 7/1980 | Zebelean |
| D267,965 S | 2/1983 | Kobayashi |
| 4,429,879 A | 2/1984 | Schmidt |
| 4,432,549 A | 2/1984 | Zebelean |
| 4,449,707 A | 5/1984 | Hayashi et al. |
| 4,451,041 A | 5/1984 | Hayashi et al. |
| 4,451,042 A | 5/1984 | Hayashi et al. |
| 4,465,221 A | 8/1984 | Schmidt |
| 4,471,961 A | 9/1984 | Masghati et al. |
| 4,489,945 A | 12/1984 | Kobayashi |
| 4,511,145 A | 4/1985 | Schmidt |
| 4,762,324 A | 8/1988 | Anderson |
| 4,792,140 A | 12/1988 | Yamaguchi et al. |
| 4,826,172 A | 5/1989 | Antonious |
| 4,842,243 A | 6/1989 | Butler |
| 4,913,438 A | 4/1990 | Anderson |
| 4,915,385 A | 4/1990 | Anderson |
| 4,915,386 A | 4/1990 | Antonious |
| 4,919,430 A | 4/1990 | Antonious |
| 4,919,431 A | 4/1990 | Antonious |
| 4,921,252 A | 5/1990 | Antonious |
| 4,928,965 A | 5/1990 | Yamaguchi et al. |
| 4,930,781 A | 6/1990 | Allen |
| 4,932,658 A | 6/1990 | Antonious |
| 4,955,610 A | 9/1990 | Creighton et al. |
| D312,858 S | 12/1990 | Anderson et al. |
| 5,000,454 A | 3/1991 | Soda |
| 5,024,437 A | 6/1991 | Anderson |
| 5,028,049 A | 7/1991 | McKeighen |
| 5,046,733 A | 9/1991 | Antonious |
| 5,056,705 A | 10/1991 | Wakita et al. |
| 5,060,951 A | 10/1991 | Allen |
| 5,067,715 A | 11/1991 | Schmidt et al. |
| 5,090,702 A | 2/1992 | Viste |
| 5,094,383 A | 3/1992 | Anderson et al. |
| 5,106,094 A | 4/1992 | Desbiolles et al. |
| 5,141,230 A | 8/1992 | Antonious |
| 5,163,682 A | 11/1992 | Schmidt et al. |
| 5,180,166 A | 1/1993 | Schmidt et al. |
| 5,183,255 A | 2/1993 | Antonious |
| 5,213,328 A | 5/1993 | Long et al. |
| 5,221,087 A | 6/1993 | Fenton et al. |
| 5,240,252 A | 8/1993 | Schmidt et al. |
| 5,242,167 A | 9/1993 | Antonious |
| 5,255,918 A | 10/1993 | Anderson et al. |
| 5,261,663 A | 11/1993 | Anderson |
| 5,261,664 A | 11/1993 | Anderson |
| 5,271,621 A | 12/1993 | Lo |
| 5,292,129 A | 3/1994 | Long et al. |
| 5,295,689 A | 3/1994 | Lundberg |
| 5,301,945 A | 4/1994 | Schmidt et al. |
| 5,318,300 A | 6/1994 | Schmidt et al. |
| 5,328,184 A | 7/1994 | Antonious |
| 5,344,140 A | 9/1994 | Anderson |
| 5,346,218 A | 9/1994 | Wyte |
| 5,351,958 A | 10/1994 | Helmstetter |
| 5,358,249 A | 10/1994 | Mendralla |
| 5,362,047 A | 11/1994 | Shaw et al. |
| 5,362,055 A | 11/1994 | Rennie |
| 5,366,223 A | 11/1994 | Werner et al. |
| 5,380,010 A | 1/1995 | Werner et al. |
| 5,390,924 A | 2/1995 | Antonious |
| 5,395,113 A | 3/1995 | Antonious |
| 5,397,126 A | 3/1995 | Allen |
| 5,401,021 A | 3/1995 | Allen |
| 5,405,136 A | 4/1995 | Hardman |
| 5,405,137 A | 4/1995 | Vincent et al. |
| 5,407,202 A | 4/1995 | Igarashi |
| RE34,925 E | 5/1995 | McKeighen |
| 5,417,419 A | 5/1995 | Anderson et al. |
| 5,417,559 A | 5/1995 | Schmidt |
| 5,423,535 A | 6/1995 | Shaw et al. |
| 5,429,357 A | 7/1995 | Kobayashi |
| 5,431,396 A | 7/1995 | Shieh |
| 5,433,440 A | 7/1995 | Lin |
| 5,447,307 A | 9/1995 | Antonious |
| 5,447,309 A | 9/1995 | Vincent |
| 5,451,056 A | 9/1995 | Manning |
| 5,460,376 A | 10/1995 | Schmidt et al. |
| 5,467,983 A | 11/1995 | Chen |
| 5,470,069 A | 11/1995 | Schmidt et al. |
| 5,474,296 A | 12/1995 | Schmidt et al. |
| 5,482,279 A | 1/1996 | Antonious |
| 5,497,993 A | 3/1996 | Shan |
| 5,505,453 A | 4/1996 | Mack |
| 5,522,593 A | 6/1996 | Kobayashi et al. |
| 5,524,331 A | 6/1996 | Pond |
| 5,533,729 A | 7/1996 | Leu |
| 5,536,006 A | 7/1996 | Shieh |
| 5,547,630 A | 8/1996 | Schmidt |
| 5,549,297 A | 8/1996 | Mahaffey |
| 5,564,994 A | 10/1996 | Chang |
| 5,584,770 A | 12/1996 | Jensen |
| 5,595,552 A | 1/1997 | Wright et al. |
| 5,611,741 A | 3/1997 | Schmidt et al. |
| 5,611,742 A | 3/1997 | Kobayashi |
| D379,393 S | 5/1997 | Kubica et al. |
| 5,626,530 A | 5/1997 | Schmidt et al. |
| 5,643,104 A | 7/1997 | Antonious |
| 5,643,108 A | 7/1997 | Cheng |
| 5,643,110 A | 7/1997 | Igarashi |
| 5,649,872 A | 7/1997 | Antonious |
| 5,651,409 A | 7/1997 | Sheehan |
| 5,655,976 A | 8/1997 | Rife |
| 5,669,827 A | 9/1997 | Nagamoto |
| 5,669,829 A | 9/1997 | Lin |
| 5,674,132 A | 10/1997 | Fisher |
| D387,113 S | 12/1997 | Burrows |
| 5,695,411 A | 12/1997 | Wright et al. |
| 5,709,614 A | 1/1998 | Horiba |
| 5,709,615 A | 1/1998 | Liang |
| 5,711,722 A | 1/1998 | Miyajima et al. |
| 5,716,292 A | 2/1998 | Huang |
| 5,718,641 A | 2/1998 | Lin |
| 5,720,673 A | 2/1998 | Anderson |
| 5,743,813 A | 4/1998 | Chen et al. |
| 5,753,170 A | 5/1998 | Muang |
| 5,755,624 A | 5/1998 | Helmstetter |
| 5,762,567 A | 6/1998 | Antonious |
| 5,766,092 A | 6/1998 | Mimeur et al. |
| 5,766,094 A | 6/1998 | Mahaffey et al. |
| 5,766,095 A | 6/1998 | Antonious |
| 5,776,011 A | 7/1998 | Su et al. |
| 5,807,190 A | 9/1998 | Krumme et al. |
| 5,827,132 A | 10/1998 | Bamber |
| RE35,955 E | 11/1998 | Lu |
| D401,652 S | 11/1998 | Burrows |
| 5,830,084 A | 11/1998 | Kosmatka |
| 5,839,975 A | 11/1998 | Lundberg |
| 5,842,934 A | 12/1998 | Ezaki et al. |
| 5,851,159 A | 12/1998 | Burrows |
| 5,863,261 A | 1/1999 | Eggiman |
| 5,873,791 A | 2/1999 | Allen |
| 5,873,795 A | 2/1999 | Wozny et al. |
| D406,294 S | 3/1999 | Burrows |
| 5,888,148 A | 3/1999 | Allen |
| 5,890,973 A | 4/1999 | Gamble |
| D411,272 S | 6/1999 | Burrows |
| 5,908,357 A | 6/1999 | Hsieh |
| 5,921,872 A | 7/1999 | Kobayashi |
| 5,931,746 A | 8/1999 | Soong |

| | | | |
|---|---|---|---|
| 5,935,019 A | 8/1999 | Yamamoto | |
| 5,938,541 A | 8/1999 | Allen et al. | |
| 5,941,782 A | 8/1999 | Cook | |
| 5,944,619 A | 8/1999 | Cameron | |
| 5,954,596 A | 9/1999 | Noble et al. | |
| D415,807 S | 10/1999 | Werner et al. | |
| 5,961,394 A | 10/1999 | Minabe | |
| 5,967,905 A | 10/1999 | Nakahara et al. | |
| 5,971,868 A | 10/1999 | Kosmatka | |
| 5,993,329 A | 11/1999 | Shich | |
| 6,007,432 A | 12/1999 | Kosmatka | |
| 6,027,416 A | 2/2000 | Schmidt et al. | |
| 6,139,445 A | 10/2000 | Werner et al. | |
| 6,143,169 A | 11/2000 | Lee | |
| 6,152,833 A | 11/2000 | Werner et al. | |
| 6,248,025 B1 | 6/2001 | Murphy | |
| 6,319,150 B1 | 11/2001 | Werner et al. | |
| 6,338,683 B1 | 1/2002 | Kosmatka | |
| 6,354,962 B1 | 3/2002 | Galloway et al. | |
| 6,368,234 B1 | 4/2002 | Galloway | |
| 6,381,828 B1 | 5/2002 | Boyce | |
| 6,390,933 B1 | 5/2002 | Galloway | |
| 6,398,666 B1 | 6/2002 | Evans et al. | |
| 6,435,982 B1 | 8/2002 | Galloway et al. | |
| 6,565,452 B2 | 5/2003 | Helmstetter et al. | |
| 6,605,007 B1 | 8/2003 | Bissonnette et al. | |
| 6,755,627 B2 | 6/2004 | Chang | |
| 7,029,403 B2 | 4/2006 | Rice et al. | |
| 7,207,898 B2 | 4/2007 | Rice et al. | |
| 7,261,643 B2 | 8/2007 | Rice et al. | |
| 7,361,099 B2 | 4/2008 | Rice et al. | |
| 7,422,527 B2 | 9/2008 | Rice et al. | |
| 7,520,819 B2 | 4/2009 | Rice et al. | |
| 7,537,528 B2 | 5/2009 | Rice et al. | |
| 7,682,262 B2 | 3/2010 | Soracco et al. | |
| 7,931,545 B2 * | 4/2011 | Soracco et al. | 473/329 |
| 2005/0026720 A1 | 2/2005 | Willett et al. | |

FOREIGN PATENT DOCUMENTS

| | | |
|---|---|---|
| GB | 2268693 A | 1/1994 |
| GB | 2331938 A | 6/1999 |
| JP | 59207169 | 11/1984 |
| JP | 61033682 | 2/1986 |
| JP | 61162967 | 7/1986 |
| JP | 61181477 | 8/1986 |
| JP | 61185281 | 8/1986 |
| JP | 61240977 | 10/1986 |
| JP | 1244770 | 9/1989 |
| JP | 02130519 | 5/1990 |
| JP | 4020357 | 1/1992 |
| JP | 4327864 | 11/1992 |
| JP | 5212526 | 8/1993 |
| JP | 05237207 | 9/1993 |
| JP | 6007487 | 1/1994 |
| JP | 06031016 | 2/1994 |
| JP | 6114126 | 4/1994 |
| JP | 6126002 | 5/1994 |
| JP | 6154367 | 6/1994 |
| JP | 6182005 | 7/1994 |
| JP | 6269518 | 9/1994 |
| JP | 8168541 | 7/1996 |
| JP | 8243194 | 9/1996 |
| JP | 8280853 | 10/1996 |
| JP | 8280854 | 10/1996 |
| JP | 8294550 | 11/1996 |
| JP | 9028842 | 2/1997 |
| JP | 9047531 | 2/1997 |
| JP | 9154985 | 6/1997 |
| JP | 9168613 | 6/1997 |
| JP | 9192270 | 7/1997 |
| JP | 9192273 | 7/1997 |
| JP | 9239077 | 9/1997 |
| JP | 9239075 | 9/1997 |
| JP | 9248353 | 9/1997 |
| JP | 9294833 | 11/1997 |
| JP | 9299519 | 11/1997 |
| JP | 10024126 | 1/1998 |
| JP | 10024128 | 1/1998 |
| JP | 10085369 | 4/1998 |
| JP | 10118227 | 5/1998 |
| JP | 10137372 | 5/1998 |
| JP | 10155943 | 6/1998 |
| JP | 10258142 | 9/1998 |
| JP | 10263121 | 10/1998 |
| JP | 10323410 | 12/1998 |
| JP | 10337347 | 12/1998 |

OTHER PUBLICATIONS

Golf Digest, Dec. 1981, p. 58-59.

"Variable Face Thickness Technology," Calloway Golf advertisement, cover and pp. 1-4, undated.

* cited by examiner

METAL WOOD CLUB WITH IMPROVED HITTING FACE

CROSS-REFERENCE TO RELATED APPLICATIONS

The present application is a continuation of U.S. patent application Ser. No. 12/729,214, filed Mar. 22, 2010 now U.S. Pat. No. 7,931,545, which is a continuation of U.S. patent application Ser. No. 11/370,542, filed Mar. 8, 2006, now U.S. Pat. No. 7,682,262, which is a continuation-in-part of U.S. patent application Ser. No. 10/911,341, filed Aug. 4, 2004, now U.S. Pat. No. 7,207,898, which is a continuation-in-part of U.S. patent application Ser. No. 10/428,061, filed May 1, 2003, now U.S. Pat. No. 7,029,403, which is a continuation-in-part of U.S. patent application Ser. No. 09/551,771, filed Apr. 18, 2000, now U.S. Pat. No. 6,605,007, the disclosures of which are incorporated herein by reference in their entireties.

FIELD OF THE INVENTION

The present invention relates to an improved golf club head. More particularly, the present invention relates to a golf club head with an improved striking face having a relatively large zone of high initial ball velocity.

BACKGROUND

The complexities of golf club design are well known. The specifications for each component of the club (i.e., the club head, shaft, grip, and subcomponents thereof) directly impact the performance of the club. Thus, by varying the design specifications, a golf club can be tailored to have specific performance characteristics.

The design of club heads has long been studied. Among the more prominent considerations in club head design are loft, lie, face angle, horizontal face bulge, vertical face roll, center of gravity, inertia, material selection, and overall head weight. While this basic set of criteria is generally the focus of golf club engineering, several other design aspects must also be addressed. The interior design of the club head may be tailored to achieve particular characteristics, such as the inclusion of hosel or shaft attachment means, perimeter weights on the club head, and fillers within hollow club heads.

Golf club heads must also be strong to withstand the repeated impacts that occur during collisions between the golf club and the golf ball. The loading that occurs during this transient event can create a peak force of over 2,000 lbs. Thus, a major challenge is designing the club face and body to resist permanent deformation or failure by material yield or fracture. Conventional hollow metal wood drivers made from titanium typically have a uniform face thickness exceeding 2.5 mm to ensure structural integrity of the club head.

Players generally seek a metal wood driver and golf ball combination that delivers maximum distance and landing accuracy. The distance a ball travels after impact is dictated by the magnitude and direction of the ball's translational velocity and the ball's rotational velocity or spin. Environmental conditions, including atmospheric pressure, humidity, temperature, and wind speed, further influence the ball's flight. However, these environmental effects are beyond the control of the golf equipment manufacturer. Golf ball landing accuracy is driven by a number of factors as well. Some of these factors are attributed to club head design, such as center of gravity and club face flexibility.

The United States Golf Association (USGA), the governing body for the rules of golf in the United States, has specifications for the performance of golf balls. These performance specifications dictate the size and weight of a conforming golf ball. One USGA rule limits the golf ball's initial velocity after a prescribed impact to 250 feet per second ±2% (or 255 feet per second maximum initial velocity). To achieve greater golf ball travel distance, ball velocity after impact and the coefficient of restitution of the ball-club impact must be maximized while remaining within this rule.

Generally, golf ball travel distance is a function of the total kinetic energy imparted to the ball during impact with the club head, neglecting environmental effects. During impact, kinetic energy is transferred from the club and stored as elastic strain energy in the club head and as viscoelastic strain energy in the ball. After impact, the stored energy in the ball and in the club is transformed back into kinetic energy in the form of translational and rotational velocity of the ball, as well as the club. Since the collision is not perfectly elastic, a portion of energy is dissipated in club head vibration and in viscoelastic relaxation of the ball. Viscoelastic relaxation is a material property of the polymeric materials used in all manufactured golf balls.

Viscoelastic relaxation of the ball is a parasitic energy source, which is dependent upon the rate of deformation. To minimize this effect, the rate of deformation must be reduced. This may be accomplished by allowing more club face deformation during impact. Since metallic deformation may be purely elastic, the strain energy stored in the club face is returned to the ball after impact thereby increasing the ball's outbound velocity after impact.

A variety of techniques may be utilized to vary the deformation of the club face, including uniform face thinning, thinned faces with ribbed stiffeners and varying thickness, among others. These designs should have sufficient structural integrity to withstand repeated impacts without permanently deforming the club face. In general, conventional club heads also exhibit wide variations in initial ball speed after impact, depending on the impact location on the face of the club. Hence, there remains a need in the art for a club head that has a larger "sweet zone" or zone of substantially uniform high initial ball speed.

SUMMARY OF THE INVENTION

According to the invention, a golf club head includes a hitting face having a central zone made of a first material, wherein the central zone has a first tensile modulus of elasticity. A second zone, concentric with the central zone, is made of a second material having a second tensile modulus of elasticity. The first tensile modulus of elasticity is higher than the second tensile modulus of elasticity.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENT

Priority U.S. Pat. No. 6,605,007, which has been incorporated herein in its entirety, discloses an improved golf club that also produces a relatively large "sweet zone" or zone of substantially uniform high initial velocity or high coefficient of restitution (COR).

COR or coefficient of restitution is a measure of collision efficiency. COR is the ratio of the velocity of separation to the velocity of approach. In this model, therefore, COR was determined using the following formula:

$$(V_{club-post} - V_{ball-post})/(V_{ball-pre} - V_{club-pre})$$

where, $V_{club-post}$ represents the velocity of the club after impact;

V ball-post represents the velocity of the ball after impact;

$V_{club-pre}$ represents the velocity of the club before impact (a value of zero for USGA COR conditions); and $V_{ball-pre}$ represents the velocity of the ball before impact.

COR, in general, depends on the shape and material properties of the colliding bodies. A perfectly elastic impact has a COR of one (1.0), indicating that no energy is lost, while a perfectly inelastic or perfectly plastic impact has a COR of zero (0.0), indicating that the colliding bodies did not separate after impact resulting in a maximum loss of energy. Consequently, high COR values are indicative of greater ball velocity and distance.

Figure 1:
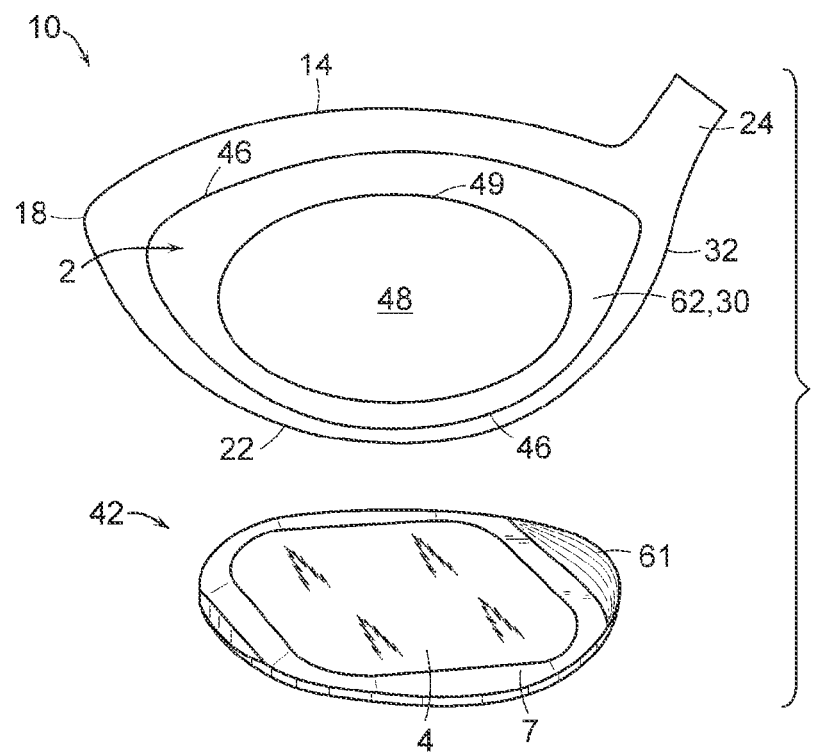
FIG. 1 is a front, exploded view of a golf club head according to the present invention as disclosed in the parent application.
Figure 2:
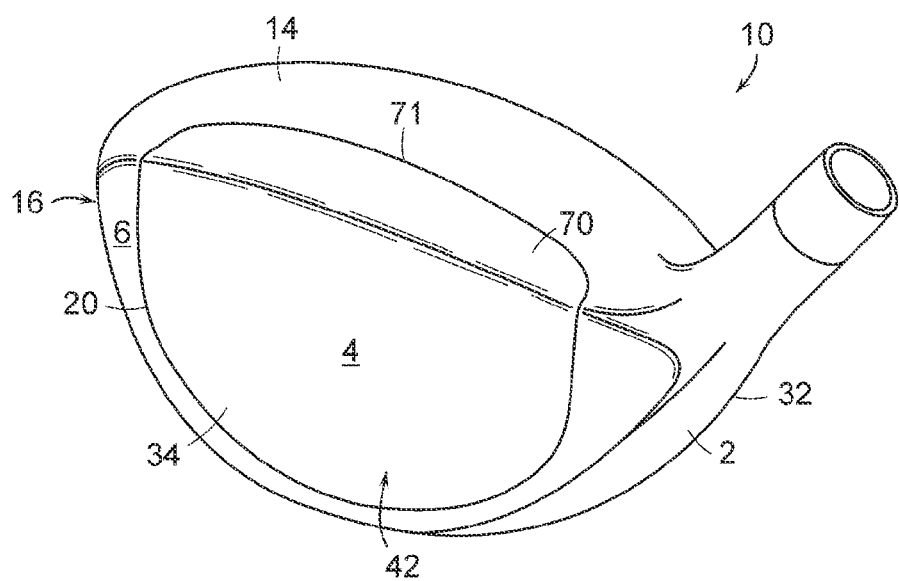
FIG. 2 is a perspective view of a golf club head according to the present invention as disclosed in the parent application.

As shown in FIG. 1, which corresponds to FIG. 2 of the parent '341 application, the accuracy of the club and the club's large zone of uniform high initial velocity are produced by hitting face 2, having central zone 4, and a surrounding intermediate zone 6, and an optional transition zone 7 between central zone 4 and intermediate zone 6. Preferably, the area of central zone 4 comprises about 15% to about 60% of the total area of the hitting face 2, and more preferably about 20% to about 50%.

Central zone 4 is comparatively rigid and intermediate zone 6 is relatively flexible so that upon ball impact, intermediate zone 6 of face 2 deforms to provide high ball velocity, while central zone 4 is substantially undeformed so that the ball flies on-target. Thus, upon ball impact the deformation of intermediate zone 6 allows central zone 4 to move into and out of a club head 10 as a unit. Surrounding intermediate zone 6 may alternatively be located directly adjacent to central zone 4. As a result, the head exhibits a coefficient of restitution greater than about 0.81.

The above is accomplished by providing central zone 4 with a first flexural stiffness and intermediate zone 6 with a second flexural stiffness. Flexural stiffness (FS) is defined as each portion's average elastic modulus (E) times each portion's average thickness (t) cubed or $$FS = Et^3 \quad \text{Eq. 1}$$

The calculation of averages of modulus and thickness is fully disclosed in the parent applications and in the '007 patent, which have previously been incorporated by reference in their entireties. The determination of FS when the thickness varies or when the material is anisotropic is also fully discussed in the parent patent applications and in the '007 patent.

Since the flexural stiffness is a function of material and thickness, the following techniques can be used to achieve the substantial difference between the flexural stiffness of central zone 4 and intermediate zone 6: 1) different materials can be used for each portion, 2) different thicknesses can be used for each portion, or 3) different materials and thickness can be used for each portion. For example, in a preferred embodiment, the thickness of the central zone is greater than the thickness of the intermediate zone and the material for both portions is the same.

In club head 10, the above flexural stiffness relationships can be achieved by selecting a certain material with a particular elastic modulus and varying the thickness of the zones. In another embodiment, the flexural stiffness relationships can be achieved by varying the materials of the zones with respect to one another so that the zones have different elastic moduli and the thickness is changed accordingly. Thus, the thickness of the zones can be the same or different depending on the elastic modulus of the material of each zone. It is also possible to obtain the required flexural stiffness ratio through the use of structural ribs, reinforcing plates, and thickness parameters. The parent applications and the '007 patent describe in detail many of these alternative structures as well as the preferred ranges of ratios of flexural stiffness between central zone 4 and intermediate zone 6.

Further, as discussed in the '007 patent, two or more different homogeneous materials may be used to form hitting face 2. For example, central zone 4 may be of generally uniform thickness and made from a stainless steel having a Young's Modulus of $30.0 \times 10^6$ lbs/in$^2$. The adjacent intermediate zone 6 has a continuously tapering thickness from the pace perimeter toward central zone 4. The thickness of intermediate zone 6 is defined to change linearly. Intermediate zone 6 is made from a titanium alloy having a Young's Modulus of $16.5 \times 10^6$ lbs/in$^2$.

Figure 3:
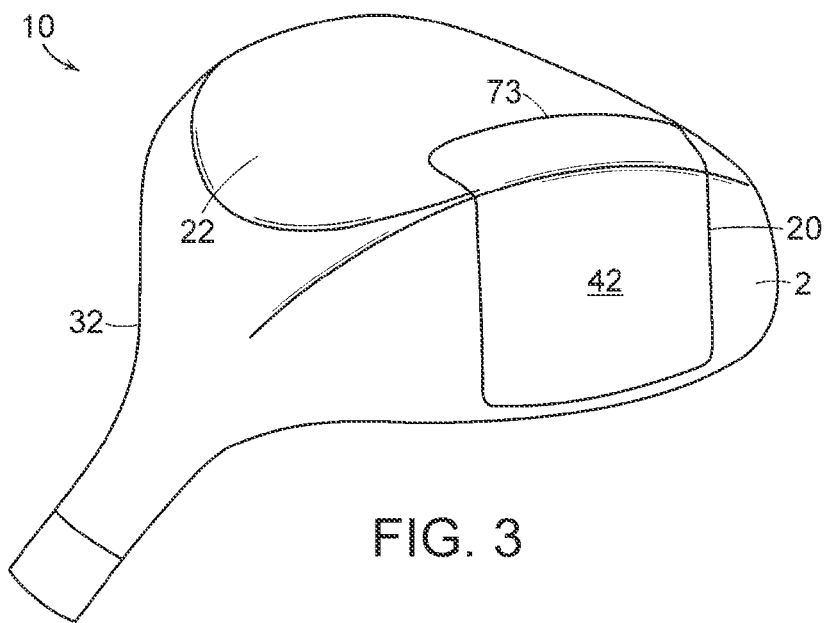
FIG. 3 is an inverted perspective view of the golf club head of FIG. 2.
Figure 4:
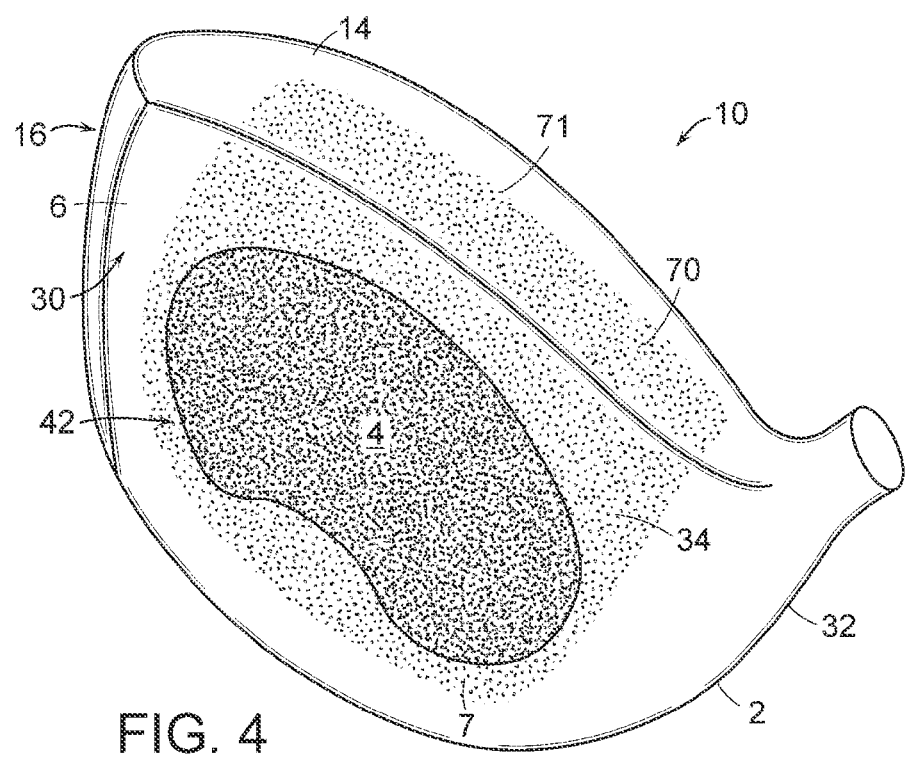
FIG. 4 is a perspective view of an alternate embodiment of a golf club head according to the present invention.
Figure 5:
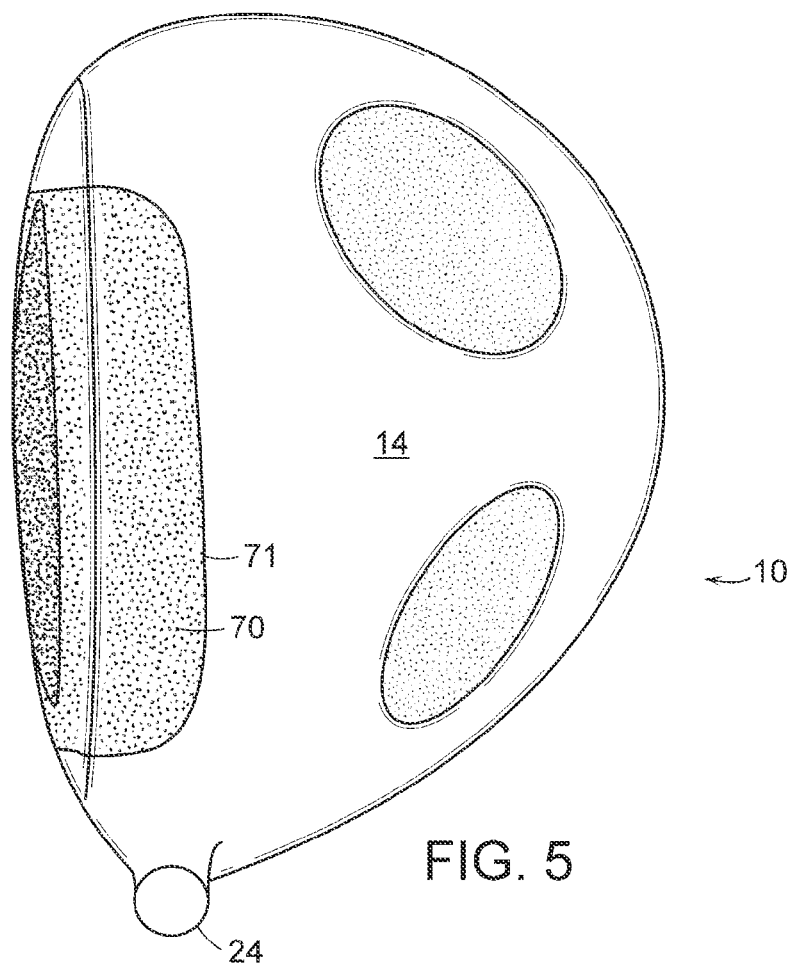
FIG. 5 is a top view of the golf club head of FIG. 4.
Figure 6:
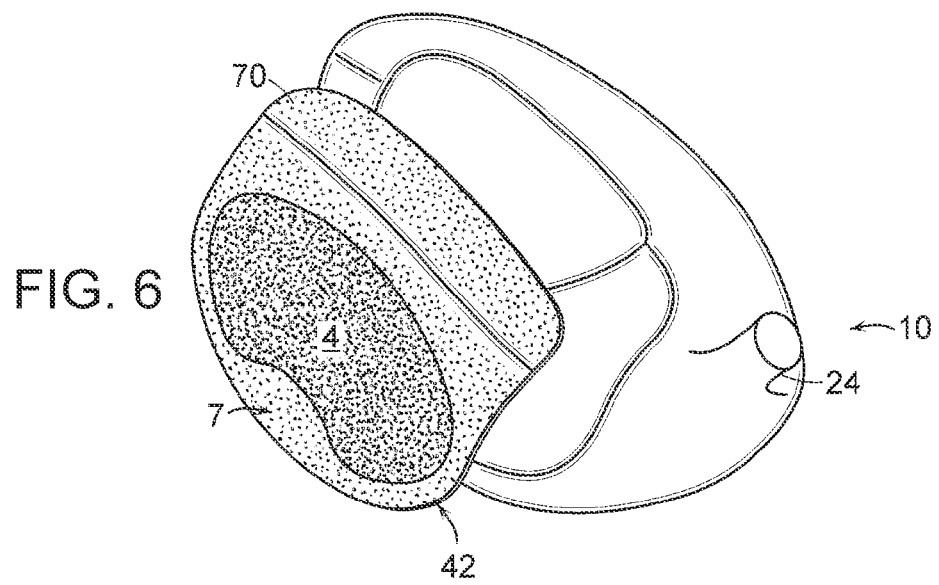
FIG. 6 is an exploded perspective view of the golf club head of FIG. 4.
Figure 7:
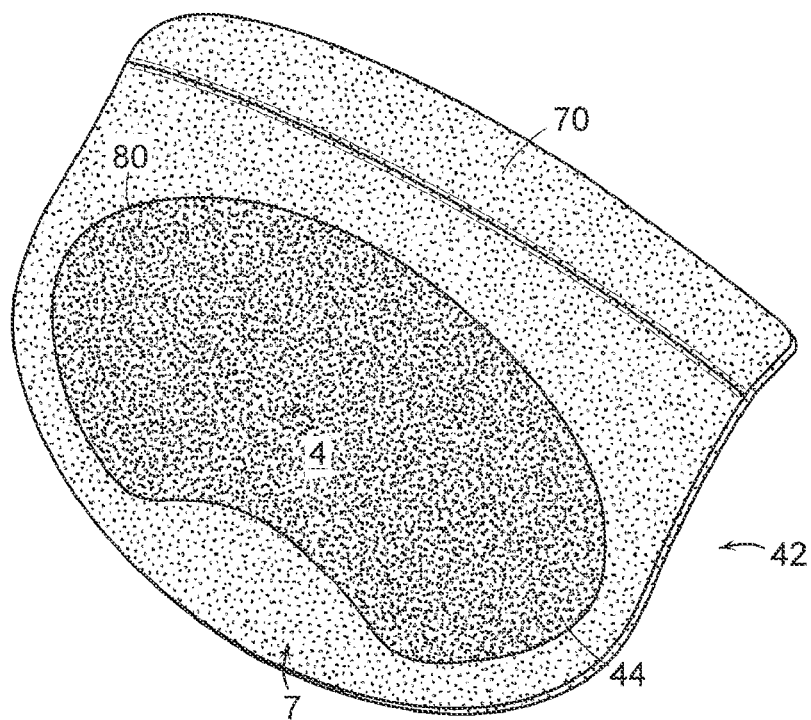
FIG. 7 is a perspective view of the hitting face of the golf club head of FIG. 4.
Figure 8:
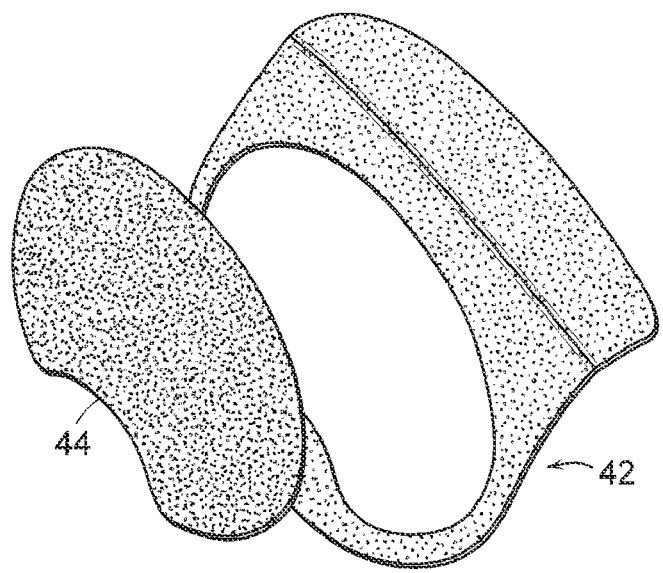
FIG. 8 is an exploded view of the hitting face of FIG. 7.

Referring now to FIGS. 2-3, another embodiment from the parent '341 application is shown. In this embodiment, central zone 4 of hitting face 2 is formed with a face insert 42. Face insert 42 is preferably welded to club head 10 along weld line 20. Face insert 42 includes a polygonal or elliptical main plate 34 and a sidewall or wing 70 that extends into and forms a part of crown 14. As such, an upper portion 71 of weld line 20 is removed to crown 14. As the stress line created by weld line 20 is removed from hitting face 2, the probability of failure along upper portion 21 due to repeated impact with golf balls is reduced.

Face insert 42 is preferably made from the same material as the rest of club head 10, such as titanium, a titanium alloy, steel, or any other material suitable for use as a club head. Face insert 42 is preferably the same thickness as the rest of club head 10, although face insert 42 may be made thicker or thinner in order to affect the flexural stiffness thereof.

The size and shape of face insert 42 may vary. As stated above, preferably, face insert 42 is a modified oval U-cup or L-cup, but it may also be other shapes, such as rectangular, elliptical or circular. Face insert 42 preferably forms nearly the entire surface area of hitting face 2. However, face insert 42 may form a much smaller portion of hitting face. Also, wing 70 may extend into and form a part of sole 22, as shown in FIG. 3, by simply inverting the configuration of face insert 42. In this case, the affected weld line is lower weld line 73.

The material properties of face insert 42 can also be affected by the method chosen to form face insert 42. For example, face insert 42 is preferably stamped from sheet metal after the metal has been cold rolled or cold worked in order to align the crystal grains of the metal. Stamping metal in this fashion produces a stronger hitting face than other manufacturing techniques. Further, face insert 42 is then positioned within hitting face 2 so that the grain flow pattern of face insert 42 runs in a sole-to-crown direction. Alternatively, the grain flow pattern of face insert 42 may run in a heel-to-toe direction or in a diagonal direction. Other methods known in the art may also be used to manufacture face insert 42, such as forging and casting.

Preferably, face insert 42 is made by milling or stamping and forming. In the manufacturing process, a malleable metal suitable for use as a hitting face, such as titanium, titanium alloy, carbon steel, stainless steel, beryllium copper, and other forgeable metals, is heated and then hammered into the desired shape of the face cup. Examples of some appropriate metals include but are not limited to titanium 6-4 alloy, titanium 15-3-3-3 alloy, titanium 20-4-1 alloy, and DAT 55 and DAT 55G, titanium alloys available from Diado Steel of Tokyo, Japan.

The preferred forging process is die or billet forging, in which a pre-measured rod of forgeable metal is heated and placed between a die, which contains the desired shape of face insert 42, and a hammer. The heated metal is then hammered into the desired shape. An advantage of forging face insert 42 is that the thickness of the face can be as thin as about 0.060 inch (or about 1.5 mm) around the perimeter or edge thereof.

Referring now to FIGS. 4-8, yet another embodiment of the present invention is shown. This embodiment combines features from both of the previously discussed embodiments, namely having a hitting face insert 42 with and a central zone insert 44 disposed in a main plate portion 34. As can be seen most clearly in FIGS. 7-8, central zone insert 44 is a generally flat piece having any shape known in the art, such as polygonal, oval, or, as shown, an irregular shape. Main plate portion 34 serves as a support to which central zone insert 44 is attached, such as by welding.

As is known in the art, a weld line or joint is an area of discontinuity, where even if two pieces of the same material are joined, the structural properties of the pieces in the vicinity of the joint are altered. Removing weld lines to the crown or the sole of a club head allows the thickness of the hitting face to be controlled more precisely and allows for a thinner overall hitting face. The joints can also be used to alter the properties of the hitting face. In accordance with this aspect of the invention, hitting face insert 42 preferably includes optional extension portions 70, 73 which may form part of crown 14 and/or part of sole 22.

Preferably, two different materials are chosen to make up hitting face insert 42. The first material is used to form central zone insert 44, and the second material is used to form the remainder of hitting face insert 42. In other words, the central zone 4 of this embodiment, similar to the central zones described above, is made of the first material, and the transition zone 7 of this embodiment, also similar to the transition zones described above, is made of the second material. The intermediate zone 6 of this embodiment is formed on a face support 30 of hitting face 2 forms, similar to the intermediate zones described above. In this embodiment, intermediate zone 6 may be made of either the first material, the second material, or a completely different material. Also, a portion of intermediate zone 6 may be located on hitting face insert 42. Central zone insert 44 may have either uniform or varying thickness, and its thickness may be the same as or different from that of hitting face insert 42.

The first alloy is chosen such that its tensile modulus of elasticity, $\epsilon_1$, is significantly greater than the tensile modulus of elasticity of the second alloy, $\epsilon_2$. Preferably, the ratio of $\epsilon_1$ to $\epsilon_2$, is a high as materially practicable. Examples of appropriate materials include titanium alloys. Preferably, the materials chosen are capable of being welded to each other.

The performance of hitting face 2 of golf club head 10, especially those that are designed to be drivers, are generally equated to the physics of plate behavior. Typical characteristics that can be expressed in a formula to assess the behavior of the plate with regard to deflections and stresses take the form of a constant known in the art from fundamental plate theory using standard assumptions to produce the following simplified equation:

$$D=\epsilon t^3/(12(1-v^2)) \qquad \text{Eq. 2}$$

where $\epsilon$ is the tensile modulus of elasticity, t is the thickness of the plate, and v is Poisson's ratio. In a preferred embodiment, where titanium alloys are used, $\epsilon$ ranges from about 70 GPa to about 128 GPa, and v ranges from about 0.33 to about 0.35. The thickness of the plate t in the present invention will vary depending upon, inter alia, manufacturing techniques and the characteristics of the material, so the club face can withstand the high and repeated impact forces from the collision with golf balls over the life of the club.

The structural behavior of the hitting face may be controlled in part by choosing alloys with different tensile moduli of elasticity. As is known in the art, the solution for the deflection w of a circular plate having radius a and loaded at its center with a point load P, is as follows:

$$w=Pa^2/(16\pi D) \qquad \text{Eq. 3}$$

Thus, the deflection w is determined, in part, by the tensile modulus of elasticity $\epsilon$ of the material of the circular plate. While hitting face insert 42 nor central zone insert 44 is a perfect circular plate, the deflection of both hitting face insert 42 and central zone insert 44 may be approximated using Eq. 3. As is known in the art, the actual deflection w of a plate having specific material properties and thickness may be determined using a variety of techniques, including Finite Element Analysis.

Alternatively, the first and second materials have different elongation and yield strengths. Preferably, central zone insert 44 is made of a first material with a very high yield strength, while main plate 34 and extension portions 70, 73 of hitting face insert 42 are made of a second material with a significantly lower yield strength. For the purposes of example only, central zone insert 44 may be made from titanium while main plate 34 and extension portions 70, 73 may be made from steel. By using a lower yield strength material, this embodiment can take advantage of the lower yield strength material's plastic deformation behavior. When impacted by a golf ball, hitting face 2 is subjected to stress due to the force of impact. Once a portion of hitting face 42 has seen a stress level beyond its yield strength, that portion elongates. As central zone insert 44 has a very high yield strength compared to the surrounding portion of hitting face 42, main plate 34 will slightly plastically deform while central zone insert 44 experiences no such plastic deformation. In essence, the periphery of main plate 34 will behave like a hinge for central zone insert 44 so that the impact stress will be redistributed to the stiffer areas of hitting face 42.

While various descriptions of the present invention are described above, it should be understood that the various features of each embodiment could be used alone or in any combination thereof. Therefore, this invention is not to be limited to only the specifically preferred embodiments depicted herein. Further, it should be understood that variations and modifications within the spirit and scope of the invention might occur to those skilled in the art to which the invention pertains. For example, the face and/or individual zones can have thickness variations in a step-wise or continuous fashion. Other modifications include a perimeter zone that has a thickness that is greater than or less than the adjacent, intermediate zone. In addition, the shapes of the central, intermediate, and perimeter zones are not limited to those disclosed herein. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

We claim:

1. A golf club head comprising:
a hitting face having a face insert coupled around a perimeter thereof to the golf club head, the hitting face comprising a central zone comprising a first material, and a second zone,
wherein the second zone is concentric with the central zone and attached to the central zone around a perimeter thereof,
wherein the second zone comprises a second material different than the first material, and
wherein the second material has an elongation that is different than the first material and the dimensions of the central zone and the second zone are selected such that the second zone deforms as a hinge to distribute impact stress to the central zone due to the impact force of striking a golf ball.

2. The golf club head of claim 1, wherein the central zone is homogeneous.

3. The golf club head of claim 2, wherein the second zone is homogeneous.

4. The golf club head of claim 1, wherein the hitting face further comprises an intermediate zone surrounding the central zone.

5. The golf club head of claim 4, wherein the intermediate zone is constructed from the first material.

6. The golf club head of claim 4, wherein the intermediate zone is constructed from the second material.

7. The golf club head of claim 4, wherein the intermediate zone is constructed from a third material that is different than the first material and the second material.

8. The golf club head of claim 1, wherein the central zone provides a central zone area that is between about 15% and about 60% of a total face area.

9. The golf club head of claim 8, wherein the central zone provides a central zone area that is between about 20% and about 50% of the total face area.

10. The golf club head of claim 1, wherein the face insert is welded to the club head.

11. The golf club head of claim 1, wherein the central zone is welded to the second zone.

12. The golf club head of claim 1, wherein the face insert further comprises a crown extension.

13. The golf club head of claim 1, wherein the face insert further comprises a sole extension.

14. The golf club head of claim 13, wherein the same material is titanium.

15. The golf club head of claim 1, wherein the first and second materials comprise alloys of the same material.

16. A golf club head comprising:
a hitting face having a face insert coupled around a perimeter thereof to the golf club head and comprising a crown extension, the hitting face comprising a central zone comprising a first material, and a second zone,
wherein the central zone provides a central zone area that is between about 20% and about 50% of the total face area,
wherein the second zone is concentric with the central zone and attached to the central zone around a perimeter thereof,
wherein the second zone comprises a second material different than the first material, and
wherein the second material has an elongation that is different than the first material and the dimensions of the central zone and the second zone are selected such that the second zone deforms as a hinge to distribute impact stress to the central zone due to the impact force of striking a golf ball.

17. The golf club head of claim 16, wherein the hitting face further comprises an intermediate zone constructed from the first material surrounding the central zone.

18. The golf club head of claim 16, wherein the hitting face further comprises an intermediate zone constructed from the second material surrounding the central zone.

19. The golf club head of claim 16, wherein the hitting face further comprises an intermediate zone constructed from a third material that is different than the first material and the second material surrounding the central zone.

20. The golf club head of claim 16, wherein the face insert further comprises a sole extension.

* * * * *